US012661521B2

(12) United States Patent
Formosa et al.

(10) Patent No.: US 12,661,521 B2
(45) Date of Patent: Jun. 23, 2026

(54) STRUCTURES AND TECHNIQUES FOR MEDICAL LEAD FABRICATION

(71) Applicant: Medtronic, Inc., Minneapolis, MN (US)

(72) Inventors: Elizabeth Formosa, Robbinsdale, MN (US); Jayesh R. Patel, Maple Grove, MN (US); Damian M. Becker, Columbia Heights, MN (US); Wen Tan, Shoreview, MN (US); Dale F. Seeley, Spring Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 248 days.

(21) Appl. No.: 18/546,700

(22) PCT Filed: Feb. 24, 2022

(86) PCT No.: PCT/US2022/017623
§ 371 (c)(1),
(2) Date: Aug. 16, 2023

(87) PCT Pub. No.: WO2022/182822
PCT Pub. Date: Sep. 1, 2022

(65) Prior Publication Data
US 2024/0131348 A1 Apr. 25, 2024
US 2024/0226586 A9 Jul. 11, 2024

Related U.S. Application Data

(60) Provisional application No. 63/153,168, filed on Feb. 24, 2021, provisional application No. 63/153,183, filed on Feb. 24, 2021.

(51) Int. Cl.
*A61N 1/375* (2006.01)
*A61N 1/05* (2006.01)
(Continued)

(52) U.S. Cl.
CPC ............. *A61N 1/3752* (2013.01); *A61N 1/05* (2013.01); *H01R 24/58* (2013.01); *H01R 43/24* (2013.01);
(Continued)

(58) Field of Classification Search
CPC ......... A61N 1/3752; A61N 1/05; H01R 24/58
(Continued)

(56) References Cited

U.S. PATENT DOCUMENTS 7,130,700 B2 10/2006 Gardeski et al.
7,890,184 B2 2/2011 Huotari et al.
(Continued)

OTHER PUBLICATIONS

Haqqani et al., "Engineering and Construction of Pacemaker and ICD Leads", Thoracic Key, Sep. 9, 2020, 11 pp., https://thoracickey.com/engineering-and-construction-of-pacemaker-and-icd-leads/.
(Continued)

*Primary Examiner* — Nadia A Mahmood
(74) *Attorney, Agent, or Firm* — Shumaker & Sieffert, P.A.

(57) ABSTRACT

In one example, a lead comprises a plurality of conductors, each conductor of the plurality of conductors comprising a conductor first end, a conductor second end, and a conductor intermediate portion therebetween, and a spline. The lead may include a first set of contacts and a second set of contracts electrically coupled with respective conductors of the plurality of conductors. The second set of contacts may include a plurality of inserts defining a plurality of apertures through which an end of respective conductors is disposed. Tire lead may further include an outer lead body disposed over at least the intermediate portion of the plurality of conductors.

20 Claims, 11 Drawing Sheets

(51) Int. Cl.
    *H01R 24/58*        (2011.01)
    *H01R 43/24*        (2006.01)
    *H01R 107/00*      (2006.01)
(52) U.S. Cl.
    CPC ...... *H01R 2107/00* (2013.01); *H01R 2201/12*
                                       (2013.01)
(58) Field of Classification Search
    USPC .......................................................... 607/2
    See application file for complete search history.

(56) References Cited

U.S. PATENT DOCUMENTS

| 7,891,085 B1 * | 2/2011 | Kuzma ................ A61N 1/0551 |
| | | 607/116 |
| 7,904,178 B2 | 3/2011 | Williams et al. |
| 7,933,662 B2 | 4/2011 | Marshall et al. |
| 8,250,754 B2 | 8/2012 | Seifert |
| 8,321,033 B2 | 11/2012 | Conger |
| 8,583,237 B2 | 11/2013 | Bedenbaugh |
| 8,634,932 B1 | 1/2014 | Ye et al. |
| 8,751,018 B1 | 6/2014 | Sethna et al. |
| 8,825,180 B2 | 9/2014 | Bauer et al. |
| 9,421,362 B2 | 8/2016 | Seeley |
| 9,962,541 B2 | 5/2018 | Howard et al. |
| 10,449,353 B2 | 10/2019 | Shoberg et al. |
| 2009/0071686 A1 | 3/2009 | Boser et al. |
| 2010/0114271 A1 | 5/2010 | Sommer et al. |
| 2010/0331934 A1 | 12/2010 | McDonald et al. |
| 2015/0088237 A1 | 3/2015 | Wechter et al. |
| 2015/0202432 A1 | 7/2015 | Somogyi et al. |
| 2017/0312500 A1 | 11/2017 | Shoberg et al. |
| 2019/0269929 A1 | 9/2019 | Bjorklund et al. |
| 2019/0321630 A1 | 10/2019 | Stone et al. |
| 2020/0129758 A1 | 4/2020 | Clemens et al. |

OTHER PUBLICATIONS

International Preliminary Report on Patentability from International Application No. PCT/US2022/017623 dated Sep. 7, 2023, 7 pp.
International Search Report and Written Opinion of International Application No. PCT/US2022/017623, dated Jun. 8, 2022, 10 pp.
U.S. Appl. No. 18/360,949, naming inventors Becker et al., filed Jul. 28, 2023.
U.S. Appl. No. 63/153,183, naming inventors Formosa et al., filed Feb. 24, 2021.

\* cited by examiner

110

140A    140B    140C    140D

140

130    178    166    120

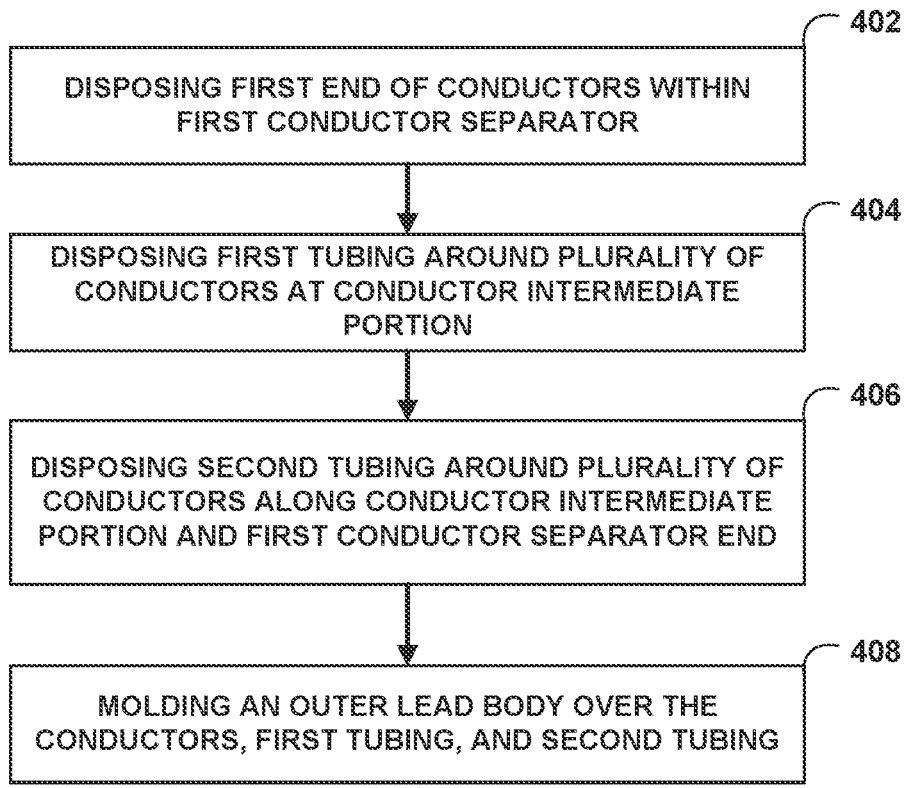

402
DISPOSING FIRST END OF CONDUCTORS WITHIN
FIRST CONDUCTOR SEPARATOR

404
DISPOSING FIRST TUBING AROUND PLURALITY OF
CONDUCTORS AT CONDUCTOR INTERMEDIATE
PORTION

406
DISPOSING SECOND TUBING AROUND PLURALITY OF
CONDUCTORS ALONG CONDUCTOR INTERMEDIATE
PORTION AND FIRST CONDUCTOR SEPARATOR END

408
MOLDING AN OUTER LEAD BODY OVER THE
CONDUCTORS, FIRST TUBING, AND SECOND TUBING

FIG. 4

STRUCTURES AND TECHNIQUES FOR MEDICAL LEAD FABRICATION

This application is a national stage entry of International Patent Application No. PCT/US2022/017623, filed Feb. 24, 2022, which claims priority to and the benefit of U.S. Provisional Patent Application No. 63/153,168, filed Feb. 24, 2021, and U.S. Provisional Patent Application No. 63/153,183, filed Feb. 24, 2021, the entire contents of Application Nos. PCT/US2022/017623, 63/153,168, and 63/153,183 are incorporated herein by reference.

TECHNICAL FIELD

The present disclosure relates to medical devices, more particularly to medical leads configured for delivering electrical signals and/or sensing electrical signals.

BACKGROUND

Implantable electrical stimulators have been proposed for use to treat a variety of symptoms or conditions, such as chronic pain, tremor, Parkinson's disease, epilepsy, urinary or fecal incontinence, sexual dysfunction, obesity, or gastroparesis. An electrical stimulator may be configured to deliver electrical stimulation therapy to a patient via one or more medical leads that include electrodes implanted proximate to a target tissue within the patient, such as a target tissue site proximate the spinal cord, pelvic nerves, peripheral nerves, or within the brain or stomach of a patient. Hence, electrical stimulation may be used in different therapeutic applications, such as deep brain stimulation (DBS), spinal cord stimulation (SCS), pelvic stimulation, gastric stimulation, or peripheral nerve stimulation. Stimulation also may be used for muscle stimulation, e.g., functional electrical stimulation (FES) to promote muscle movement or prevent atrophy.

Electrical stimulation may be delivered via one or more implanted or percutanous leads, each lead carrying one or more electrodes. The electrodes may take the form of, e.g., ring electrodes, cuff electrodes, paddle electrodes, segmented ring electrodes. Leads may be constructed, for example, by welding each electrode to a conductor (e.g., a wire) disposed within a lead body of the lead. When completed, an electrical signal generated by the electrical stimulator may be transmitted through one or more conductors and respective electrodes of the lead to generate an electrical field within the patient.

SUMMARY

In general, the disclosure is directed to devices, systems, and techniques for fabricating a medical lead, which may include multiple electrodes. The devices, systems, and techniques allow for conductor separation for election isolation, which assists in improving impedance values for the lead. This disclosure relates to implantable medical leads and components of the leads and installation of those component during manufacturing. Some leads have higher numbers of electrodes, such as 8 electrodes each with independent wires that run from the respective electrodes to contacts on the proximal end of the lead. Electrical separation of the wires, or conductors, can be done via insulation on the wires and/or other separation devices at certain locations along the lead. For example, a spline may be located at the distal end of the lead near the electrodes, and a spacer may be used at a proximal end of the lead. In some examples, a conductor separator such as a spline may be located at both the proximal and distal ends of the lead. In addition, heat shrink tubing may be provided over the transition of the proximal end of the spline and middle portion of the lead to relieve stress. Such heat shrink tubing may also enable injection molding of both ends of the lead at the same time because the heat shrink tubing retains the positions of the conductors.

In one example, this disclosure describes a lead assembly includes a plurality of conductors, each conductor of the plurality of conductors comprising a conductor first end, a conductor second end, and a conductor intermediate portion therebetween; a spline extending from a spline first end to a spline second end, the spline defining conductor channels therein, the spline defining a stylet lumen, the conductor first end of each conductor of the plurality of conductors disposed within respective conductor channels of the conductor channels; a first set of contacts electrically coupled with respective conductors of the plurality of conductors at the conductor first end; a second set of contacts electrically coupled with respective conductors of the plurality of conductors at the conductor second end, the second set of contacts comprising a plurality of inserts defining a plurality of apertures through which the second end of respective conductors are disposed; and an outer lead body disposed over at least the intermediate portion of the plurality of conductors.

In another example, this disclosure describes a lead assembly includes a plurality of conductors, each conductor of the plurality of conductors comprising a conductor first end, a conductor second end, and a conductor intermediate portion therebetween; a spline extending from a spline first end to a spline second end, the spline defining conductor channels therein, the spline defining a stylet lumen, the conductor first end of each conductor of the plurality of conductors disposed within respective conductor channels of the conductor channels; a first set of contacts electrically coupled with respective conductors of the plurality of conductors at the conductor first end; a second set of contacts electrically coupled with respective conductors of the plurality of conductors at the conductor second end, the second set of contacts comprising a plurality of inserts defining a plurality of apertures through which the second end of respective conductors are disposed; a first tubing disposed around the plurality of conductors at a portion of the conductor intermediate portion, the first tubing disposed between the conductor and the outer lead body; a second tubing disposed around the spline second end and a portion of the plurality of the conductors extending away from the spline second end; and an outer lead body disposed over at least the intermediate portion of the plurality of conductors.

In another example, this disclosure describes a method that includes disposing conductors within a spline, a spline extending from a spline first end to a spline second end, the spline having conductor channels, the spline defining a stylet lumen, conductors extending from a conductor first end to a conductor second end and having a conductor intermediate portion therebetween; disposing the conductors includes disposing the conductor first end of the conductors within the conductor channels; electrically coupling a first set of contacts with the conductors at the conductor first end; disposing the conductor second end of each of the plurality of conductors through respective apertures of the second set of contacts; electrically coupling each of the plurality of conductors with the respective second set of contacts; and disposing an outer lead body over the conductors.

In another example, this disclosure describes a method that includes disposing a plurality of conductors within a first conductor separator, the first conductor separator extending from a first separator first end to a first separator second end, the first separator defining first conductor channels, the first separator defining a stylet lumen, conductors extending from a conductor first end to a conductor second end and having a conductor intermediate portion therebetween; disposing the conductors within the first conductor separator includes disposing the conductor first end of the conductors within the first conductor channels; electrically coupling a first set of contacts with the conductors at the conductor first end; electrically coupling a second set of contacts with the conductors at the conductor second end; disposing a first tubing around the plurality of conductors along a portion of the conductor intermediate portion; disposing a second tubing around the plurality of conductors along a portion of the conductor intermediate portion and the first separator second end; and molding an outer lead body over the conductors, over the first tubing, over the second tubing, between the first set of contacts, and between the second set of contacts.

In another example, this disclosure describes a lead assembly that includes conductors extending from a conductor first end to a conductor second end and having a conductor intermediate portion therebetween; a first conductor separator extending from a first conductor separator proximal end to a first conductor separator distal end, the first conductor separator having first conductor channels, the first conductor separator having a stylet lumen, the first conductor separator having the conductor first end of the conductors disposed within the first conductor channels; a first set of contacts electrically coupled with the conductors at the conductor first end; a second set of contacts electrically coupled with the conductors at the conductor second end, the second set of contacts comprising insert molded contacts; a first tubing disposed around a portion of the conductor intermediate portion, wherein the first tubing is heat-shrink tubing; an outer lead body molded over the conductors, the first tubing, between the first set of contacts, and between the second set of contacts; the first set of contacts are disposed at a distal end and the second set of contacts are disposed at a promixal end of the lead assembly; a second tubing disposed around the first conductor separator distal end and conductors; and wherein the second tubing is heat-shrink tubing, and the second tubing overlaps a portion of the first tubing.

The details of one or more examples are set forth in the accompanying drawings and the description below. Other features, objects, and advantages will be apparent from the description, drawings, and claims.

BRIEF DESCRIPTION OF DRAWINGS

The details of the present disclosure are set forth in the accompanying drawings and the description below. Other features, objects, and benefits will be apparent from the description and drawings, and from the claims.

FIG. 4 is a flow diagram for a method of assembly in accordance with one or more techniques of this disclosure.

DETAILED DESCRIPTION

Figure 1A:
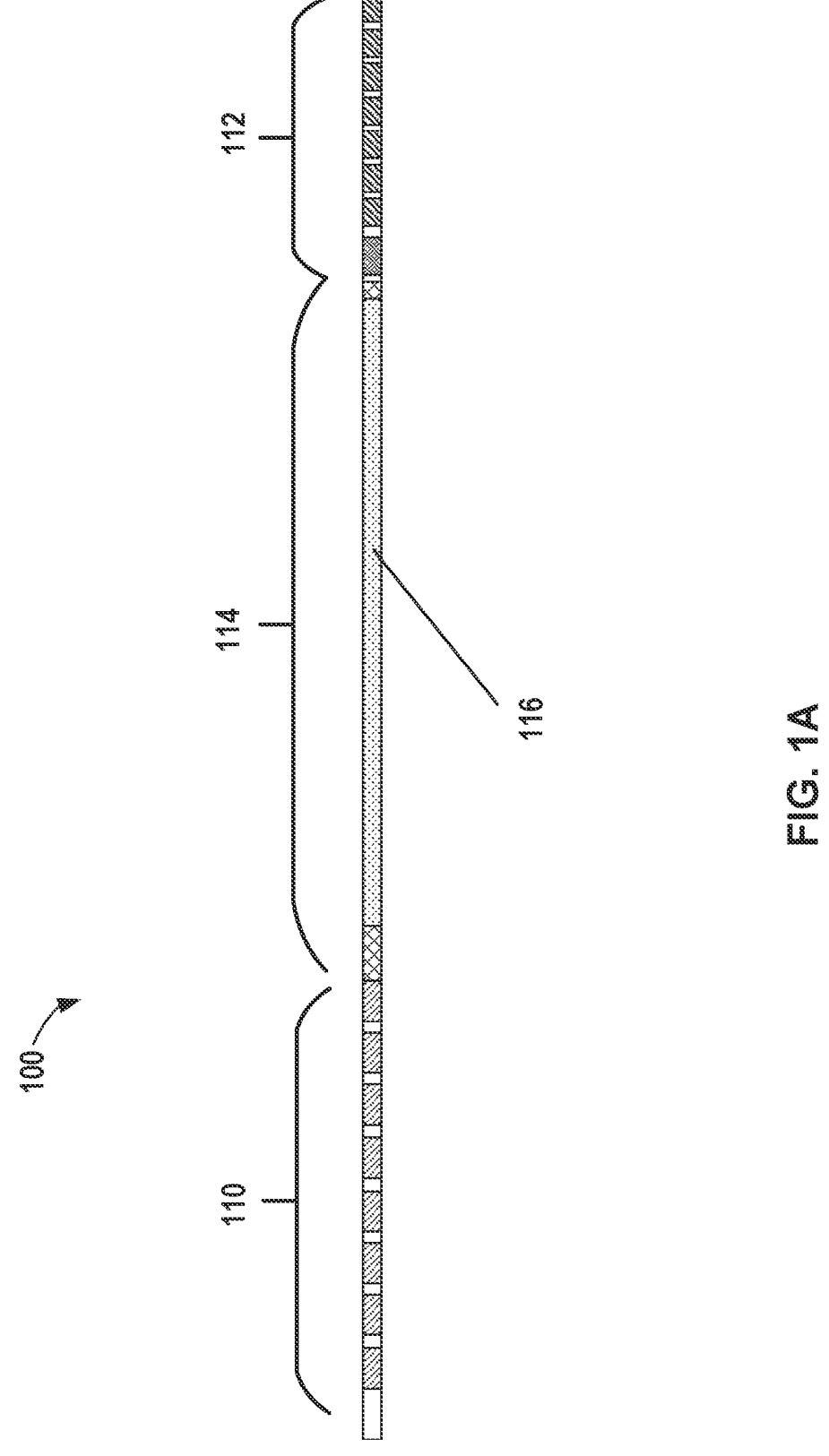
FIG. 1A is a conceptual diagram illustrating an example medical lead with ring electrodes.

Devices, systems, and techniques for fabricating a medical lead with one or more electrodes are described herein. In some examples of electrical stimulation therapy, a therapy system includes a medical device configured to generate electrical stimulation signals and a medical lead to deliver or transfer the stimulation signals to the patient. The lead may include one or more electrodes (e.g., disposed on a longitudinal surface, distal tip, or both of the lead) configured to deliver the electrical stimulation signals to the patient.

As disclosed herein, various structures and techniques may be utilized to electrically isolate the conductors, which may improve impedance values. As leads become more sophisticated, impedance requirements have increased, as well as the need to better isolate conductors, connectors, and electrodes. Increasing the isolation of the conductors, connectors, and electrodes may improve impedance characteristics, increase control over electrode alignment, facilitate lead assembly with higher densities of electrodes, and decrease lead variability (e.g., variability between leads of the same type).

Electrical separation of the wires, or conductors, can be done via insulation on the wires and/or other separation devices at certain locations along the lead. For example, a spline may be located at the distal end of the lead near the electrodes, and a spacer may be used at a proximal end of the lead. In some examples, a conductor separator such as a spline may be located at both the proximal and distal ends of the lead. In addition, heat shrink tubing may be provided over the transition of the proximal end of the spline and middle portion of the lead to relieve stress. Such heat shrink tubing may also enable injection molding of both ends of the lead at the same time because the heat shrink tubing retains the positions of the conductors.

The leads described herein may be used to deliver a variety of electrical stimulation therapies to a patient. In one example, the lead may be used to deliver neurostimulation therapy to a patient's brain, e.g., DBS. However, the features and techniques described herein are useful in other types of medical device systems, which may include other types of implantable medical leads and implantable medical devices. For example, the fabrication devices and techniques described herein may be used to fabricate cardiac leads for cardiac rhythm management devices (e.g., pacemakers or pacemaker-cardioverter-defibrillators). As other examples, the features and techniques described herein may be used for leads that deliver other types of neurostimulation therapy (e.g., spinal cord stimulation or vagal stimulation), stimulation of at least one muscle or muscle groups, stimulation of at least one organ such as gastric system stimulation, stimulation concomitant to gene therapy, and, in general, stimulation of any tissue of a patient.

In addition, leads described herein may be coupled at their proximal ends to a stimulation therapy controller (e.g., an implantable medical device) located remotely from the electrodes, but other configurations are also possible and contemplated. For example, a lead may be defined, at least in part, by a portion of a housing (e.g., a medical device housing) or a member coupled to a housing of a medical device. In another example, the lead may even include a stimulation generator, e.g., a microstimulator, located proximate to or at the stimulation site. In other examples, a lead may include a member at a stimulation site that is wirelessly coupled to an implanted or external stimulation controller or generator. The processes, devices, and systems described herein for fabricating a medical lead may be used with any medical device that includes electrodes may disposed on a surface of the device.

As described herein, axial, radial, and circumferential directions refer to a cylindrical coordinate system with respect to the lead that is being fabricated. In other words, the axial direction is the longitudinal direction parallel with a center axis defined by the lead. The radial direction is the direction orthogonal to or at a right angle to the center axis. In other words, the radial direction extends directly away from the center axis. The circumferential direction refers to the angular position or direction around the outer surface of the lead. Different circumferential positions with respect to the lead may vary by some angle centered at the center axis.

FIGS. 1A-2D illustrate example leads that may be fabricated in accordance with the processes, devices, and systems described herein. FIG. 1A is a conceptual diagram illustrating an example medical lead 100, that includes a first lead end 110, a lead body 114 portion, and a second lead end 112, where the lead body 114 is between the first lead end 110 and the second lead end 112. In some examples, the first lead end 110 is a distal lead end configured to be disposed in contact with tissue of a patient. In one or more examples, the second lead end 112 is a proximal lead end configured to be coupled with an implantable medical device. Lead 100 may include contacts, such as ring electrodes or segmented ring electrodes. As shown in FIG. 1A and FIG. 1E, lead 100 may include outer lead body 114 and a first set of contacts 130 which may include contacts 130A, 130B, 130C, 130D, 130E, 130F, 130G, and 130I (collectively referred to as "contacts 130"). In one more examples, the first set of contacts 130 are disposed at a first, for example distal, lead end 110, and may be configured to contact tissue. The lead 100 may further include a second set of contacts 150, as shown in FIG. 1H, which may include contacts 150A, 150B, 150C, 150D, 150E, 150F, 1500, and 1501 (collectively referred to as "contacts 150"). In one or more examples, the second set of contacts 150 are disposed at a proximal end of the lead 100 and may be configured to be connected to an implantable medical device. In one or more examples, the second set of contacts 150 are electrically coupled with the implantable medical device.

Figure 1B:
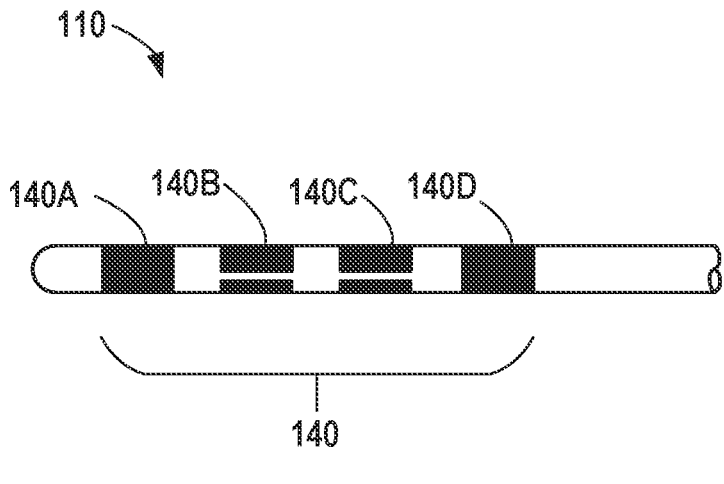
FIG. 1B is a conceptual diagram illustrating an example medical lead with four segmented ring electrodes in each electrode level.

In one or more examples, the first set of contacts 130 may comprise electrodes such as ring electrodes at the different electrode levels. FIG. 1B illustrates another example of the first lead end 110 which may include segmented electrodes 140 for the first set of contacts 130. In the example shown in FIG. 1B, electrode levels 140A and 140D each includes a single ring electrode within the respective level. Electrode levels 140B and 140C each includes three segmented ring electrodes disposed at different positions around a perimeter of the lead. Lead 100 having electrode levels as shown in FIG. 1B may be referred to as a "1-3-3-1" lead because each electrode level comprises one, three, three, and one electrode, respectively.

Lead 100 may also be described as including a complex electrode array geometry. A complex electrode array geometry may be an electrode array that includes at least one level of segmented ring electrodes (e.g., circumferentially positioned electrodes). In another example, a complex electrode array geometry may refer to an electrode array that includes electrodes centered in two, three, or even more planes. A complex electrode geometry may indicate any electrode array in which different electrode combinations may be used to deliver electrical stimulation in multiple directions away from the lead. Thus, the complex electrode array geometry may include multiple levels of segmented ring electrodes, segmented ring electrodes and ring electrodes, or any other combination of electrodes including at least one level of segmented ring electrodes. Segmented ring electrodes may generally be two or more electrodes located at different angular or circumferential positions around the circumference of lead body 114. Segmented ring electrodes or other complex electrode array geometries may be used to produce customizable stimulation fields (e.g., electrical fields that may affect or activate patient tissue) that may be directed to a particular side of lead 100 in order to isolate the stimulation field around the target anatomical region of a brain in DBS, for example.

Lead 100 may have any suitable configuration. Lead 100 may be substantially cylindrical (e.g., cylindrical or nearly cylindrical) in shape (e.g., may have a circular or nearly circular cross-section when the cross-section is taken in a direction perpendicular to a longitudinal axis of lead 100). In other examples, however, lead 100 may have another suitable shape. For example, lead 100 may define one or more curves, e.g., a shape configured to reach target anatomical regions of the patient. In some examples, lead 100 may be similar to a flat paddle lead or a conformable lead shaped for the patient. Also, in other examples, lead 100 may for constructed of any of a variety of different polygonal cross sections taken transverse to the longitudinal axis of the lead. Although lead 100 may be generally flexible, a lead may include one or more portions that are semi-rigid or rigid to aid in implantation and/or achieve desired orientation of lead 100 within the patient.

Outer lead body 116 may be formed from an insulative biocompatible material. Example biocompatible materials may include at least one of polyurethane, silicone, and fluoropolymers such as tetrafluroethylene (ETFE), polytetrafluroethylene (PTFE), and/or expanded PTFE (i.e. porous ePTFE, nonporous ePTFE). Outer lead body 116 may be a molded lead body that at least partially surrounds a lead structure that supports the electrodes and plurality of conductors (e.g., electrically conductive wires) that electrically couple to respective electrodes of lead 100. In some examples, outer lead body 116 may be injection molded.

Figure 1C:
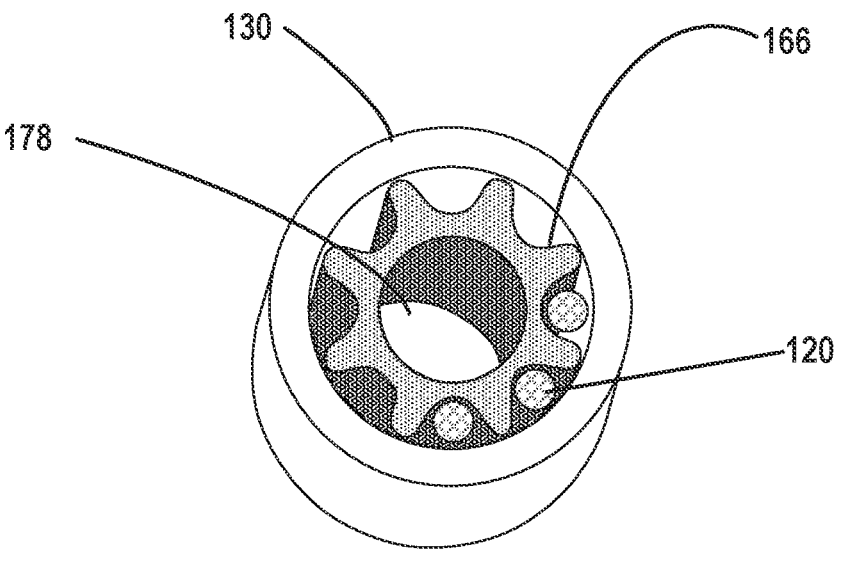
FIG. 1C is a cross-section of the lead of FIG. 1A at the distal end of the lead.

Within outer lead body 116, lead 100 may also include a plurality of conductors 120, such as insulated electrical conductors, as shown in FIGS. 1C, ID, IF, 1G, and IH. In some examples, the plurality of conductors may each include a respective insulation sheath. In some examples, the conductors may have SI polyamide insulation. In some examples, the insulation may enable direct welding between an electrode and a conductor without separate ablation of the insulation. In some examples, the welding process may burn through the insulation as it combines the metals together.

The conductors 120 may extend from a conductor first end 124 (FIG. 1H) to a conductor second end 126 (FIG. 1G), and have a conductor intermediate portion 128 therebetween. In one or more examples, the outer lead body 116 is disposed over at least the conductor intermediate portion 128. In some examples, the conductors 120 terminate at the respective contacts. For example, the conductor first end 124 may be within a contact 130, and the conductor second end 126 may be within a contact 150.

Figure 1D:
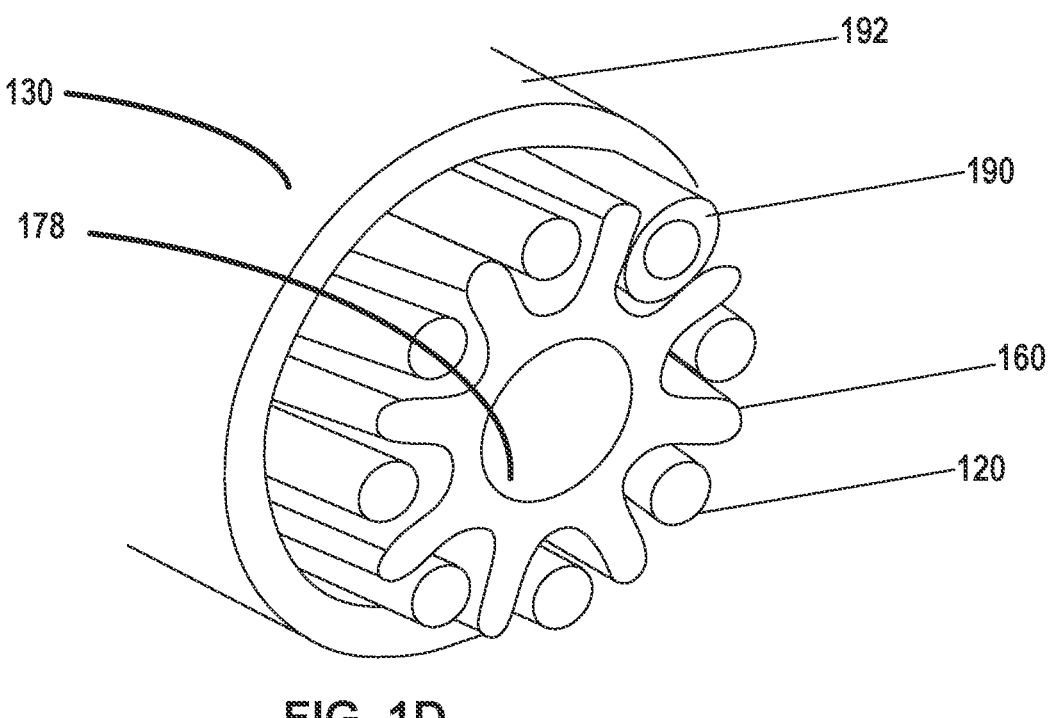
FIG. 1D is a cross-section of the lead of FIG. 1A at the distal end of the lead.
Figure 1E:
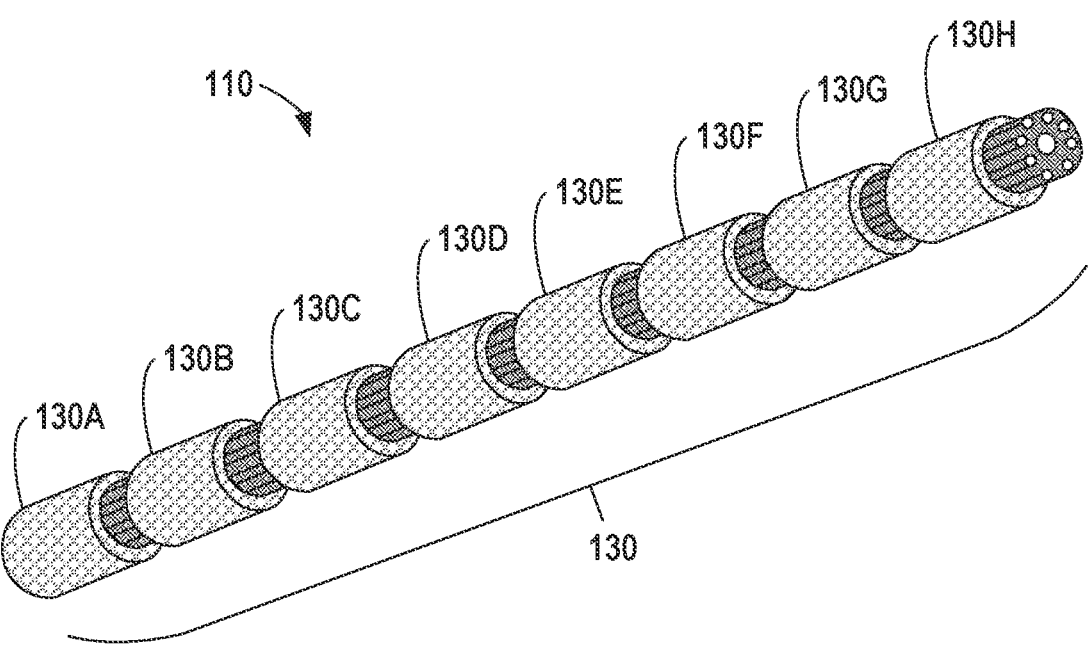
FIG. 1E is a conceptual diagram of a electrodes disposed along the distal end of the lead.

The plurality of conductors may each be coupled to at least one contact of a first and second set of contacts 130, 150, where the contacts 130, 150 may include electrodes. For example, a first set of contacts 130 may be electrically coupled with respective conductors of the plurality of conductors 120 at the conductor first end 124. In some examples, the conductors 120 may include a crimp tube 190, as shown in FIG. 1D, and the conductor may be laser welded at 192 to electrically connect the conductors 120 with an inner surface of the contacts 130.

In some examples, a second set of contacts 150 may be electrically coupled with respective conductors of the plurality of conductors 120 at the conductor second end 124. In some examples, the second set of contacts 150 may include a plurality of inserts 196 defining a plurality of apertures through which the second end 126 of respective conductors are disposed. For example, the second set of contacts 150 may include pre-molded insert rings. The insert rings may be disposed at the first lead end 110 and/or the second lead end 112. In one or more examples, the conductors 120 may include a crimp tube 194. In some examples the conductor is welded with the inserts 196. In some examples, the pre-molded inserts have a hardness of 75D.

In some examples, the conductors may be coiled along part or all of the length of lead body 114 (e.g., in a multiconductor coil). In other examples, the conductors may be substantially straight instead of coiled. In either case, the conductors may be straightened or curved at their distal end (e.g., near their respective electrode) to be mechanically coupled to an electrode.

Figure 3:
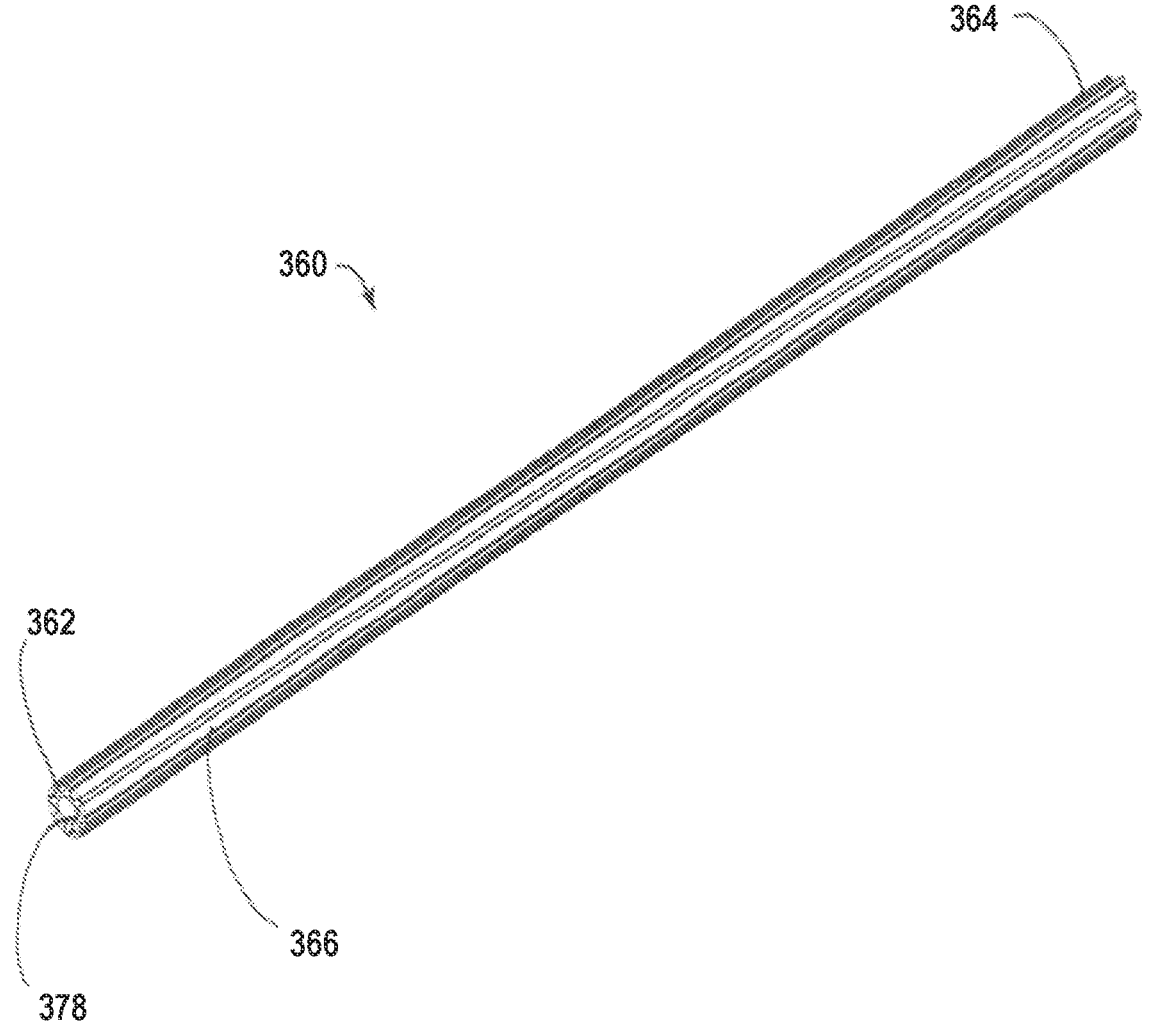
FIG. 3 is a conceptual diagram of an example spline.

In one or more examples, lead 100 further includes a spline 360, where the spline 360 may extend from a spline proximal end 362 to a spline distal end 364, as shown in FIG. 3. In some examples, in reference to FIG. 1C the spline may define conductor channels 166 therein. In some examples, the conductor channels 166 extend from the spline proximal end 162 to the spline distal end 164. The conductor channels 166 are sized and configured to receive conductors 120 therein. In some examples, the conductor first end 124 of each conductor of the plurality of conductors 120 is disposed within respective conductor channels of the conductor channels 166. In some examples, the spline 160 may be a straight spline, or may be twisted spline. In one or more examples, the spline 160 may be a nine-lumen spline which may have eight conductor channels 166 and a stylet lumen 178, as shown in FIGS. 1C and 1D. In one or more examples, the spline 160 may be disposed at the lead distal end. In one or more examples, the spline 160 may be disposed along the lead body 114, for example with channels for conductors along the lead body 114. In one or more examples, the spline 160 may be disposed at the lead proximal end 110.

In one or more examples, the spline may define a stylet lumen 178 therein, where the stylet lumen 178 may be sized and configured to receive a stylet therethrough. In some examples, the spline 160 may have a predetermined hardness. In one or more examples, the spline 160 may have a first hardness at the spline proximal end 162 and a second hardness at the spline distal end 164, where the first hardness may be different than the second hardness. In some examples, the first hardness may be greater than the second hardness. In some examples, the second hardness may be greater than the first hardness. In some examples, the spline 160 may have a 55D stiffness. In some examples, spline 166 is softer than the pre-molded inserts 196.

Figure 1F:
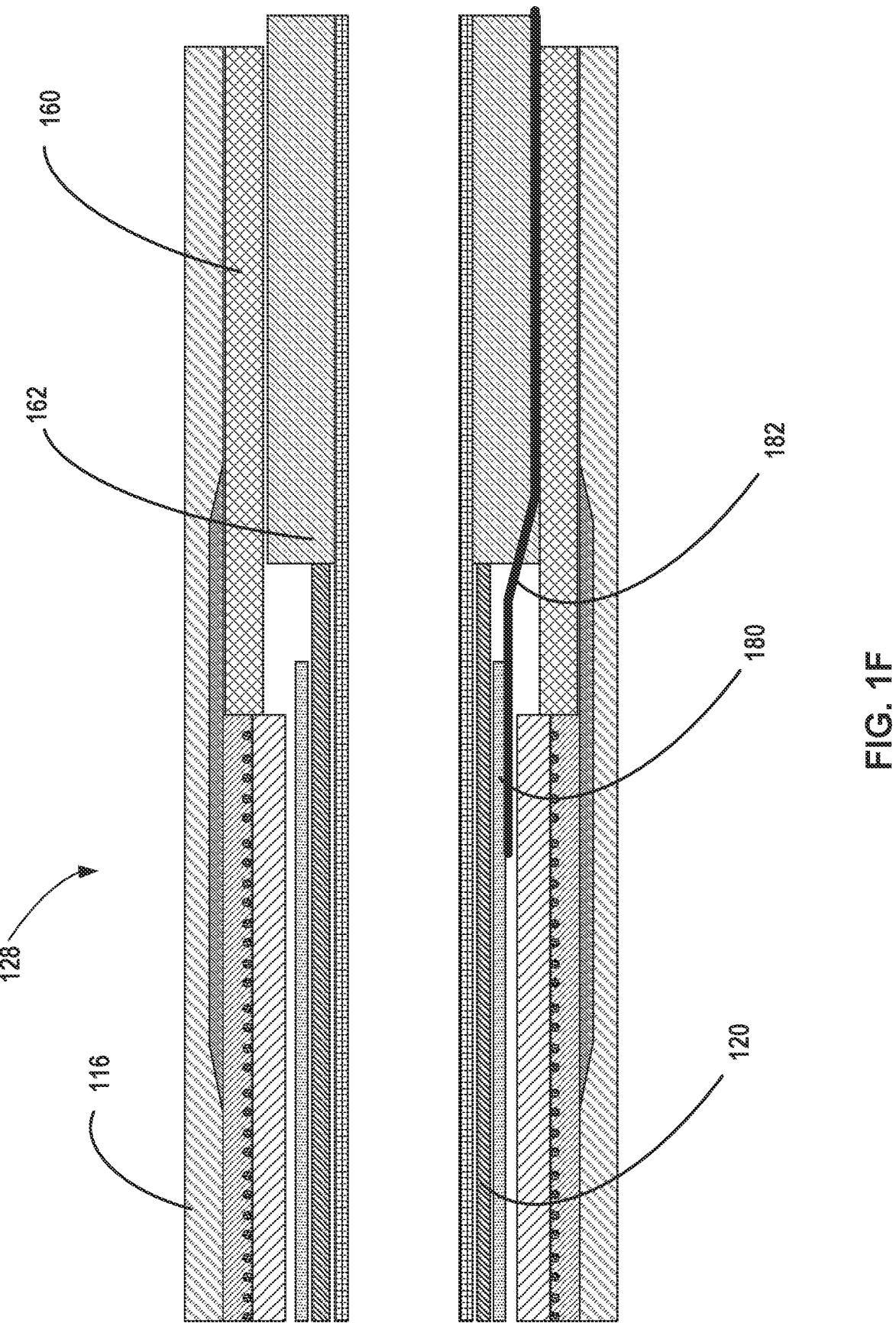
FIG. 1F is a cross-section of the lead of FIG. 1A at the distal end of the lead.
Figure 1G:
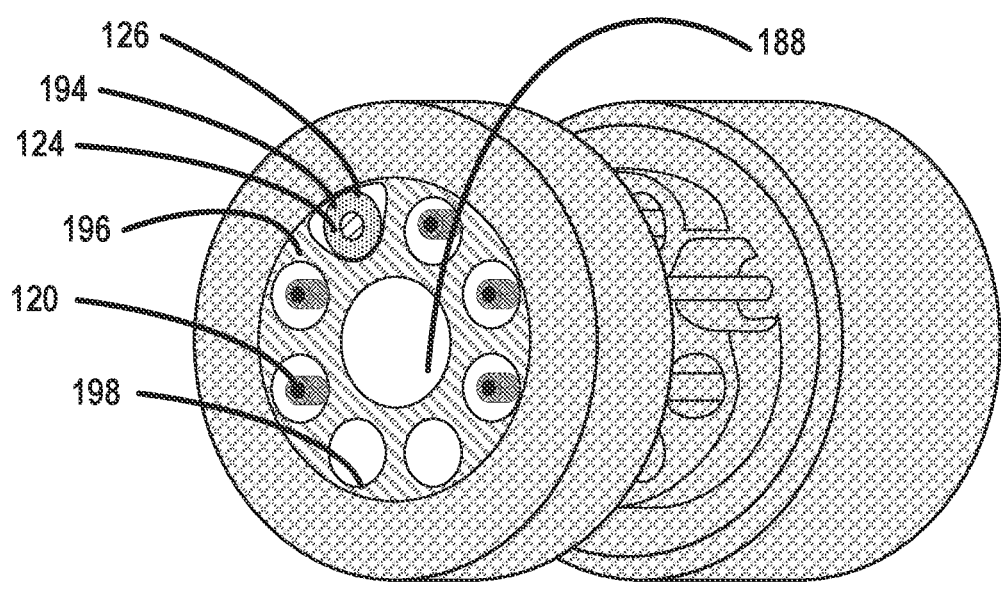
FIG. 1G is a cross-section of the lead of FIG. 1A at the proximal end of the lead.
Figure 1H:
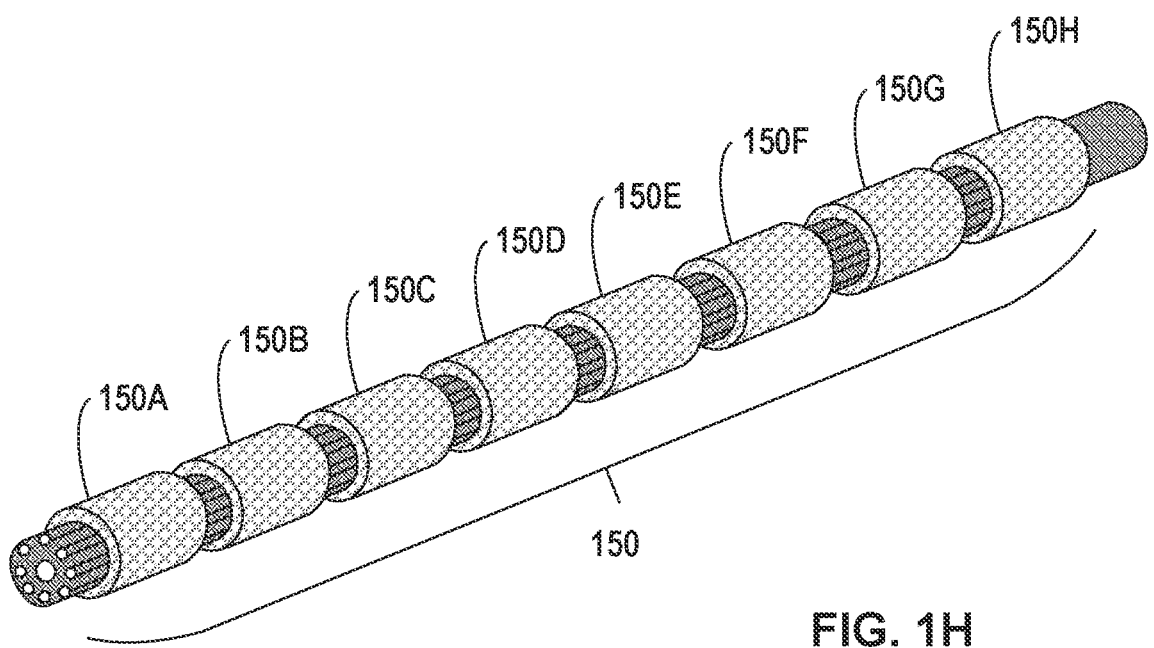
FIG. 1H is a conceptual diagram of a electrodes disposed along the proximal end of the lead.

In some examples, referring to FIG. 1F, a first tubing 180 is disposed around the plurality of conductors 120 at a portion of the conductor intermediate portion 128, where the first tubing 180 is disposed between the plurality of conductors 120 and the outer lead body 116. In some examples, a second tubing 182 may be disposed around the spline first end 162 and around a portion of the plurality of the conductors 120 extending away from the spline distal end 164 towards a lead proximal end. In one or more examples, at least a portion the second tubing 182 may overlap a portion of the first tubing 180, as shown in FIG. 1F. In some examples, a portion of the first tubing 180 may be disposed within the second tubing 182. In some examples, the first tubing 180 and/or the second tubing 182 may be heat-shrink tubing. In one or more examples, a portion of the second tubing 182 may be connected with, such as my heat shrinking techniques, to the first tubing 180.

A method of forming a lead is further described herein. In one or more examples, conductors may be disposed within conductor channels of a spline, where a first end of the conductors may be disposed within the channels of the spline. The method may further include electrically coupling a first set of contacts with the conductors, for example a conductor first end. The method may include disposing a conductor second end of each of the plurality of conductors through respective apertures of the second set of contacts, where the apertures may be within insert molded contact ring. The plurality of conductors may be electrically coupled with the second set of contacts. The method may include disposing an outer lead body over the conductors.

In one or more examples, a first tubing, such as heat-shrink tubing, may be disposed around a portion of the conductor intermediate portion, the heat-shrink tubing may be heated. In some examples, a second tubing, such as heat-shrink tubing, may be disposed around a portion of the conductor intermediate portion, and the heat-shrink tubing may be heated. In one or more examples, the second tubing may be disposed over at least a portion of the first tubing, and the second tubing may overlap a portion of the first tubing.

In some examples, the outer lead body may be injection molded over the conductors. For instance, an operator may place the assembled lead (without the outer lead body) into a mold form. The operator may then begin to introduce (e.g., via injection) the polymer, or material, into mold form. The injected material may surround any exposed portions of conductors, welds, first tubing, second tubing, and lead structures, but typically does not cover external portions of the contacts.

Although some examples of leads described herein include splines or insert rings, other examples, may include coiled conductors along the entire length of the lead from proximal to distal end. This type of multiconductor coil may include many conductors within the coil, such as more than 4 conductors, which may include 6 conductors, 8 conductors, or more. Each conductor of the multiconductor coil may be configured to be coupled to a respective electrode (e.g., to deliver stimulation or sense electrical signals) at the distal end of the lead and a respective connector at the proximal end of the lead (e.g., to electrically connect the conductor to an IMD). Therefore, an 8 conductor coil lead may include 8 electrodes at the distal end and 8 connectors at the proximal end. Since each conductor may be in a coil shape through the entire length of the lead, the lead body may be manufactured by injection molding the lead body. The very proximal and distal ends of each conductor may be straightened or otherwise moved from the coil shape to be electrically coupled to the respective electrode or connector. Each conductor may be covered by insulation, which may be SI polyamide insulation as described herein. Using SI polyamide insulation may enable direct welding between an electrode (or connector) and a conductor without separate ablation of the insulation. In some examples, the welding process may burn through the insulation as it combines the metals together.

Figure 2A:
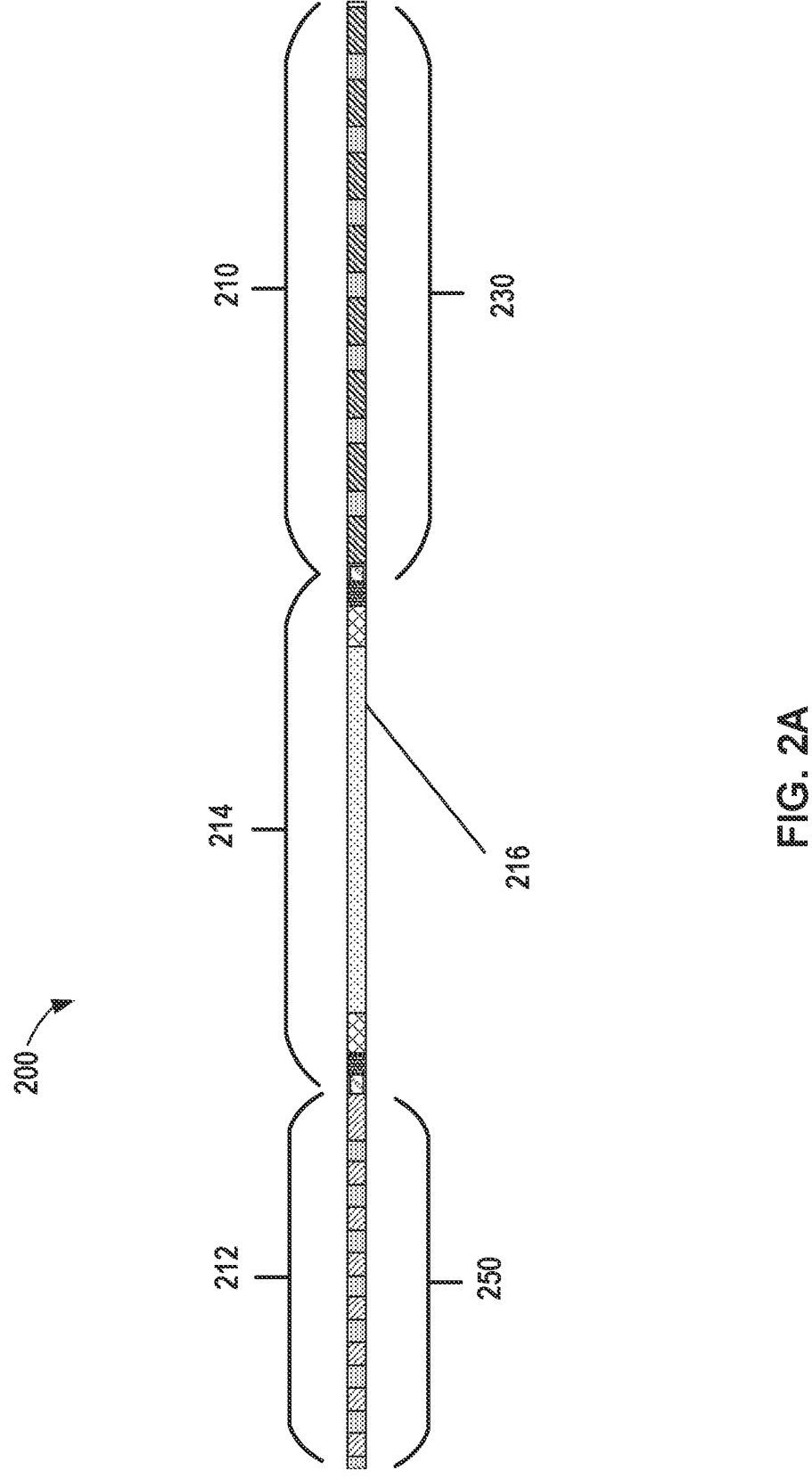
FIG. 2A is a conceptual diagram illustrating an example medical lead with ring electrodes.

FIG. 2A is a conceptual diagram illustrating an example medical lead 200, that includes a first lead end 210, a lead body 214 portion, and a second lead end 212, where the lead body 214 is between the first lead end 210 and the second lead end 212. In some examples, the first lead end 210 is a distal lead end configured to be disposed in contact with tissue of a patient. In one or more examples, the second lead end 212 is a proximal lead end configured to be coupled with an implantable medical device. Lead 200 may include contacts, such as ring electrodes or segmented ring electrodes. As shown in FIG. 2A, lead 200 may include outer lead body 214 and a first set of contacts 230 which may include eight contacts. In one more examples, the first set of contacts 230 are disposed at a first, for example distal, lead end 210, and may be configured to contact tissue of a patient. The lead 200 may further include a second set of contacts 250. In one or more examples, the second set of contacts 250 are disposed at a proximal end of the lead 200 and may be configured to be connected to an implantable medical device. In one or more examples, the second set of contacts 230 are electrically coupled with the implantable medical device.

Figure 2B:
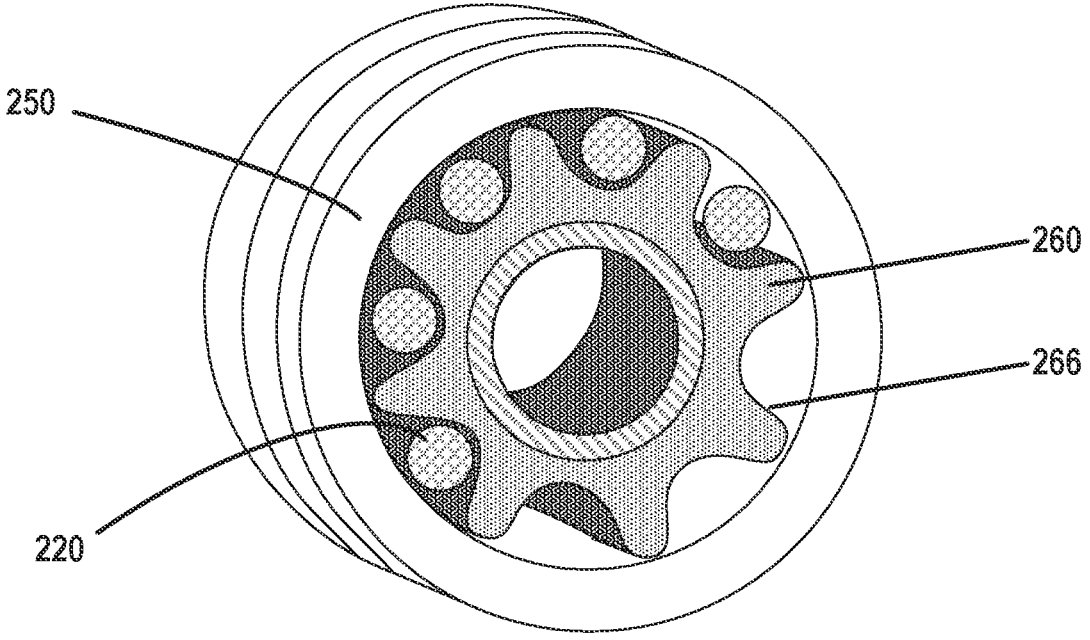
FIG. 2B is a cross-section of the lead of FIG. 2A at the proximal end of the lead.

In one or more examples, the first set of contacts 230 may comprise electrodes such as ring electrodes at the different electrode levels. FIG. 2B illustrates another example of the first lead end 210 which may include segmented electrodes for the first set of contacts 230. The segmented electrodes may be similar to the segmented electrodes discussed above for FIG. 1B.

Lead 200 may also be described as including a complex electrode array geometry. A complex electrode array geometry may be an electrode array that includes at least one level of segmented ring electrodes (e.g., circumferentially positioned electrodes). In another example, a complex electrode array geometry may refer to an electrode array that includes electrodes centered in two, three, or even more planes. A complex electrode geometry may indicate any electrode array in which different electrode combinations may be used to deliver electrical stimulation in multiple directions away from the lead. Thus, the complex electrode array geometry may include multiple levels of segmented ring electrodes, segmented ring electrodes and ring electrodes, or any other combination of electrodes including at least one level of segmented ring electrodes. Segmented ring electrodes may generally be two or more electrodes located at different angular or circumferential positions around the circumference of lead body 214. Segmented ring electrodes or other complex electrode array geometries may be used to produce customizable stimulation fields (e.g., electrical fields that may affect or activate patient tissue) that may be directed to a particular side of lead 200 in order to isolate the stimulation field around the target anatomical region of a brain in DBS, for example.

Lead 200 may have any suitable configuration. Lead 200 may be substantially cylindrical (e.g., cylindrical or nearly cylindrical) in shape (e.g., may have a circular or nearly circular cross-section when the cross-section is taken in a direction perpendicular to a longitudinal axis of lead 200). In other examples, however, lead 200 may have another suitable shape. For example, lead 200 may define one or more curves, e.g., a shape configured to reach target anatomical regions of the patient. In some examples, lead 200 may be similar to a flat paddle lead or a conformable lead shaped for the patient. Also, in other examples, lead 200 may for constructed of any of a variety of different polygonal cross sections taken transverse to the longitudinal axis of the lead. Although lead 200 may be generally flexible, a lead may include one or more portions that are semi-rigid or rigid to aid in implantation and/or achieve desired orientation of lead 200 within the patient.

Outer lead body 216 may be formed from an insulative biocompatible material. Example biocompatible materials may include at least one of polyurethane, silicone, and fluoropolymers such as tetrafluroethylene (ETFE), polytetrafluroethylene (PTFE), and/or expanded PTFE (i.e. porous ePTFE, nonporous ePTFE). Outer lead body 216 may be a molded lead body that at least partially surrounds a lead structure that supports the electrodes and plurality of conductors (e.g., electrically conductive wires) that electrically couple to respective electrodes of lead 200. In some examples, outer lead body 216 may be injection molded.

Figure 2C:
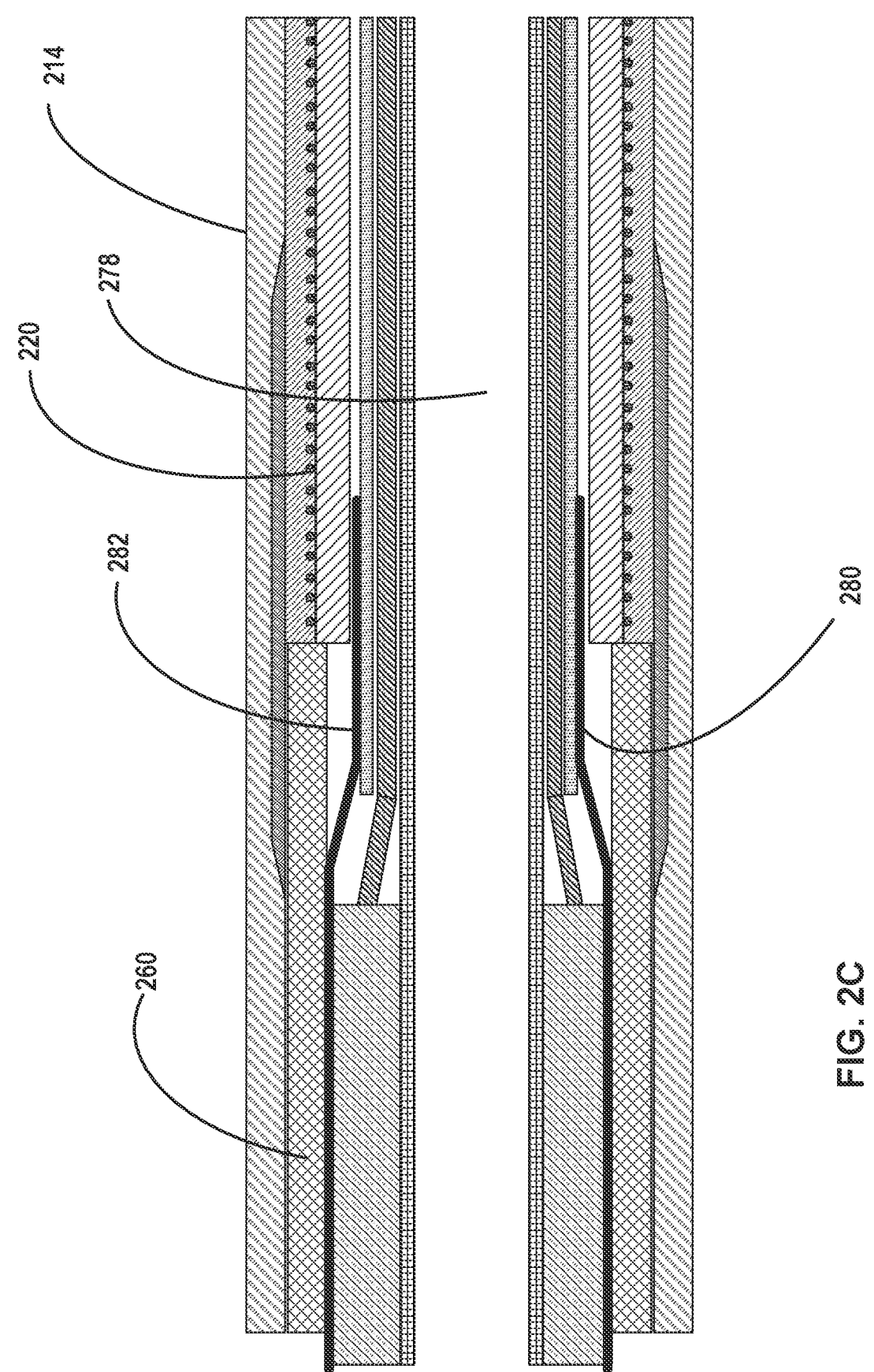
FIG. 2C is a cross-section of the lead of FIG. 2A at the proximal end of the lead.
Figure 2D:
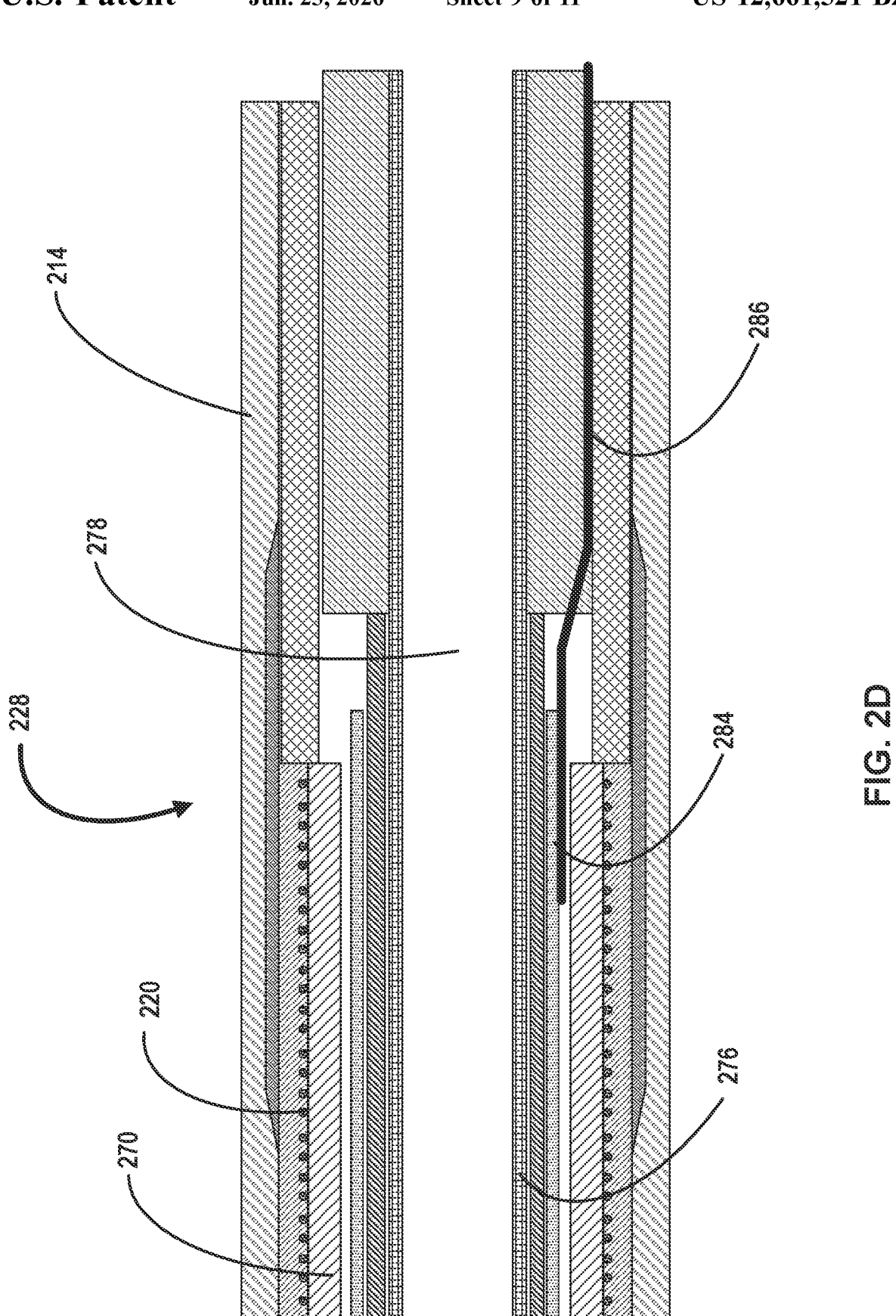
FIG. 2D is a cross-section of the lead of FIG. 2A at the distal end of the lead.

Within outer lead body 216, lead 200 may also include a plurality of conductors 220, such as insulated electrical conductors, as shown in FIGS. 2B, 2C, and 2D. In some examples, there are eight conductors and eight contacts at each end of the lead 200. In some examples, the plurality of conductors may each include a respective insulation sheath. In some examples, the conductors may have SI polyamide insulation. The conductors 220 may extend from a conductor first end to a conductor second end, and have a conductor intermediate portion therebetween. In one or more examples, the outer lead body 216 is disposed over at least the conductor intermediate portion 228. In some examples, the conductors 220 terminate at the respective contacts. For example, the conductor first end 224 may be within a contact 230, and the conductor second end 226 may be within a contact 250.

The plurality of conductors may each be coupled to at least one contact of a first and second set of contacts 230, 250, where the contacts 230, 250 may include electrodes. For example, a first set of contacts 230 may be electrically coupled with respective conductors of the plurality of conductors 220 at the conductor first end 224. In some examples, the conductors 220 may include a crimp tube 290, as shown in FIG. 2D, and the conductor may be laser welded at 292 to electrically connect the conductors 220 with the contacts 230. In some examples, the conductors 220 may be insulated. In some examples, the welding process may burn through the insulation as it combines the metals together.

In some examples, a second set of contacts 250 may be electrically coupled with respective conductors of the plurality of conductors 220 at the conductor second end 224. In one or more examples, the conductors 220 may include a crimp tube and the conductor may be laser welded to electrically connect the conductors 220 with the contacts 250. In some examples, the conductors 220 may be insulated. In some examples, the welding process may burn through the insulation as it combines the metals together.

In some examples, the conductors may be coiled along part or all of the length of lead body 214 (e.g., in a multiconductor coil). In other examples, the conductors may be substantially straight instead of coiled. In either case, the conductors may be straightened or curved at their distal end (e.g., near their respective electrode) to be mechanically coupled to an electrode.

In one or more examples, lead 200 further includes structure, such as a first conductor separator 260 (FIG. 2B) and a second conductor separator 270 (FIG. 2D), that separates the leads from one another. For example, lead 200 may include a spline 360, where the spline 360 may extend from a spline proximal end 362 to a spline distal end 364, as shown in FIG. 3. In some examples, in reference to FIG. 2C the conductor separator may define conductor channels 266 therein. For example, the conductor separators 260, 270 may include longitudinally disposed fins that maintain the conductors separated from each other within the lead. In some examples, the conductor channels 266 extend from the conductor separator first end 262 to the conductor separator second end 264. The conductor channels 266 are sized and configured to receive conductors 220 therein.

In some examples, the conductor first end 224 of each conductor of the plurality of conductors 220 is disposed within respective conductor channels of the conductor channels 266. In some examples, the first and second conductor separators 260, 270 may be a straight spline, or may be twisted spline. In one or more examples, the first and second conductor separators 260, 270 may be a nine-lumen spline which may have eight conductor channels 266 and a stylet lumen 278, as shown in FIGS. 2C and 2D. In one or more examples, the first and second conductor separators 260, 270 may be disposed at the lead distal end. In one or more examples, the spline 260 may be disposed at the lead proximal end 210. In one or more examples, first and second conductor separators 260, 270 are disposed at the lead proximal end and the lead distal end.

In one or more examples, the first and second conductor separators 260, 270 may each be an eight channel extruded tube. In some examples, a cross section of the spline may have a gear shape, for example, as shown in FIG. 2B. In some examples, the first and second conductor separators 260, 270 may have a predetermined hardness. In one or more examples, the first conductor separator 260 may have a first hardness at the second end of the lead 212 and the second conductor separator 260 may have a second hardness at the first end of the lead 210, where the first hardness may be different than the second hardness. In some examples, the second hardness may be greater than the first hardness. In some examples, the first conductor separator 260 may have a 55D stiffness, and/or may be formed of 55D polyurethane. In some examples, the second conductor stiffness may have a second stiffness of 75D, and/or may be formed of 75D polyurethane.

In one or more examples, the first and second conductor separators 260, 270 may define a center stylet lumen 278 therein, where the stylet lumen 278 may be sized and configured to receive a stylet therethrough. In one or more examples a stylet coil 276 is disposed within the stylet lumen 278. In some examples, a thin tube may fit over the stylet coil, and the thin tube and stylet coil 276 fit within the stylet lumen 278, as shown in FIG. 2D. In some examples, the thin tube may have a wall thickness between 0.0001 and 0.0002 inches. In some examples, the thin tube may be molded, heat shrink, film cast, or extruded.

In some examples, referring to FIG. 2C, a first tubing 280 may be disposed around the plurality of conductors 220 at a portion of the conductor intermediate portion 228. In some examples, the first tubing 280 may abut or be disposed adjacent to an end of the first conductor separator 260, and may further be disposed over the stylet coil.

In some examples, a second tubing 282 may be disposed around an end of the conductor separator 260, such as a second end, and around a portion of the plurality of the conductors 220 at the conductor intermediate portion 228. In one or more examples, at least a portion the second tubing 282 may overlap a portion of the first tubing 280. In some examples, a portion of the first tubing 280 may be disposed within the second tubing 282. In some examples, the first tubing 280 and/or the second tubing 282 may be heat-shrink tubing. In one or more examples, a portion of the second tubing 282 may be connected with, such as my heat shrinking techniques, to the first tubing 280. In some examples, the first and second tubing 280, 282 may provide joint strength and/or allow injection molding of the lead body.

In some examples, referring to FIG. 2D, a third tubing 284 may be disposed around the plurality of conductors 220 at a portion of the conductor intermediate portion 228. In some examples, the third tubing 284 may abut or be disposed adjacent to an end of the second conductor separator 270, such as a second end, and may further be disposed over the stylet coil.

In some examples, a fourth tubing 286 may be disposed around an end, such as a second end of the second conductor separator 270, and around a portion of the plurality of the conductors 220. In one or more examples, at least a portion the fourth tubing 286 may overlap a portion of the third tubing 284. In some examples, a portion of the third tubing 284 may be disposed within the fourth tubing 286. In some examples, the third tubing 284 and/or the fourth tubing 286 may be heat-shrink tubing. In one or more examples, a portion of the fourth tubing 286 may be connected with, such as my heat shrinking techniques, to the third tubing 284. In some examples, the third and fourth tubing 284, 286 may provide joint strength and/or allow injection molding of the lead body.

A method of forming a lead is further described herein as shown in FIG. 4. In one or more examples, the method may include disposing a plurality of conductors within a first conductor separator, the first conductor separator extending from a first separator first end to a first separator second end, the first separator defining first conductor channels, the first separator defining a stylet lumen, conductors extending from a conductor first end to a conductor second end and having a conductor intermediate portion therebetween. In some examples, the method may further include disposing the plurality of conductors in a second conductor separator, the second conductor separator extending from a second conductor separator first end to a second conductor separator second end, the second conductor separator having second conductor channels, wherein disposing the conductors in the second conductor separator may include disposing the conductor second end of the conductors within the second conductor channels.

In some examples, disposing the conductors within the first conductor separator may include disposing the conductor first end of the conductors within the first conductor channels (402) In some examples, the method may include electrically coupling a first set of contacts with the conductors at the conductor first end, and electrically coupling a second set of contacts with the conductors at the conductor second end. In some examples, the method may include disposing a first tubing, such as heat-shrink tubing, around the plurality of conductors along a portion of the conductor intermediate portion (404), and disposing a second tubing, such as heat-shrink tubing, around the plurality of conductors along a portion of the conductor intermediate portion and the first separator second end (406). In some examples, disposing the second tubing around a portion of the conductor intermediate portion may include disposing the second tubing over the first tubing and the second tubing overlaps a portion of the first tubing.

The following examples are described herein.

Example 1. A lead assembly comprising: a plurality of conductors, each conductor of the plurality of conductors comprising a conductor first end, a conductor second end, and a conductor intermediate portion therebetween; a spline extending from a spline first end to a spline second end, the spline defining conductor channels therein, the spline defining a stylet lumen, the conductor first end of each conductor of the plurality of conductors disposed within respective conductor channels of the conductor channels; a first set of contacts electrically coupled with respective conductors of the plurality of conductors at the conductor first end; a second set of contacts electrically coupled with respective conductors of the plurality of conductors at the conductor second end, the second set of contacts comprising a plurality of inserts defining a plurality of apertures through which the second end of respective conductors are disposed; and an outer lead body disposed over at least the intermediate portion of the plurality of conductors.

Example 2. The lead assembly of example 1, wherein the first set of contacts are disposed at a distal end of the lead assembly and configured to contact tissue and the second set of contacts are disposed at a proximal end of the lead assembly and configured to be connected to an implantable medical device.

Example 3. The lead assembly of any of examples 1-2, further comprising a first tubing disposed around the plurality of conductors at a portion of the conductor intermediate portion, the first tubing disposed between the conductor and the outer lead body.

Example 4. The lead assembly of example 3, wherein the first tubing comprises heat-shrink tubing.

Example 5. The lead assembly of any of examples 3-4, further comprising a second tubing disposed around the spline second end and a portion of the plurality of the conductors extending away from the spline second end.

Example 6. The lead assembly of example 5, wherein the second tubing comprises heat-shrink tubing.

Example 7. The lead assembly of example 5, wherein at least a portion of the second tubing overlaps a portion of the first tubing.

Example 8. The lead assembly of any of examples 1-7, wherein each conductor of the plurality of conductors comprises a respective insulation sheath.

Example 9. The lead assembly of any of examples 1-8, wherein the first set of contacts comprise ring electrodes.

Example 10. The lead assembly of any of examples 1-8, wherein the first set of contacts comprise segmented electrodes, wherein the segmented electrodes comprise electrodes disposed at different positions around a perimeter of the lead assembly.

Example 11. A lead assembly comprising: a plurality of conductors, each conductor of the plurality of conductors comprising a conductor first end, a conductor second end, and a conductor intermediate portion therebetween; a spline extending from a spline first end to a spline second end, the spline defining conductor channels therein, the spline defining a stylet lumen, the conductor first end of each conductor of the plurality of conductors disposed within respective conductor channels of the conductor channels; a first set of contacts electrically coupled with respective conductors of the plurality of conductors at the conductor first end; a second set of contacts electrically coupled with respective conductors of the plurality of conductors at the conductor second end, the second set of contacts comprising a plurality of inserts defining a plurality of apertures through which the second end of respective conductors are disposed; a first tubing disposed around the plurality of conductors at a portion of the conductor intermediate portion, the first tubing disposed between the conductor and the outer lead body; a second tubing disposed around the spline second end and a portion of the plurality of the conductors extending away from the spline second end; and an outer lead body disposed over at least the intermediate portion of the plurality of conductors.

Example 12. The lead assembly of example 11, wherein the second tubing overlaps a portion of the first tubing.

Example 13. The lead assembly of any of examples 11-12, wherein the first tubing comprises heat-shrink tubing.

Example 14. The lead assembly of any of examples 11-13, wherein the second tubing comprises heat-shrink tubing.

Example 15. A method comprising: disposing conductors within a spline, a spline extending from a spline first end to a spline second end, the spline having conductor channels, the spline defining a stylet lumen, conductors extending from a conductor first end to a conductor second end and having a conductor intermediate portion therebetween; disposing the conductors includes disposing the conductor first end of the conductors within the conductor channels; electrically coupling a first set of contacts with the conductors at the conductor first end; disposing the conductor second end of each of the plurality of conductors through respective apertures of the second set of contacts; electrically coupling each of the plurality of conductors with the respective second set of contacts; and disposing an outer lead body over the conductors.

Example 16. The method of example 15, wherein the first set of contacts are disposed at a distal end and configured to contact tissue and the second set of contacts are disposed at a proximal end of the lead assembly and configured to contact an implantable medical device.

Example 17. The method of any of examples 15-16, further comprising disposing a first heat-shrink tubing around a portion of the conductor intermediate portion, and heating the first heat shrink tubing.

Example 18. The method of example 17, further comprising disposing a second heat-shrink tubing around a portion of the conductor intermediate portion, and heating the second heat shrink tubing.

Example 19. The method of example 18, wherein disposing the second heat-shrink tubing around a portion of the conductor intermediate portion includes disposing the second heat-shrink tubing over the first heat-shrink tubing and the second tubing overlaps a portion of the first tubing.

Example 20. The method of any of examples 15-19, further comprising molding an outer lead body over the conductors, over the first tubing, between the first set of electrodes, and between the second set of electrodes.

In one or more examples, a third tubing, such as heat-shrink tubing, may be disposed around a portion of the conductor intermediate portion, the heat-shrink tubing may be heated. In some examples, a fourth tubing, such as heat-shrink tubing, may be disposed around a portion of the conductor intermediate portion and the second conductor separator, and the heat-shrink tubing may be heated. In one or more examples, the second tubing may be disposed over at least a portion of the first tubing, and the second tubing may overlap a portion of the first tubing.

In some examples, the outer lead body may be injection molded over the conductors. For example, the method may include molding an outer lead body over the conductors, over the first tubing, over the second tubing, between the first set of contacts, and between the second set of contacts (408).

For instance, an operator may place the assembled lead (without the outer lead body) into a mold form. The operator may then begin to introduce (e.g., via injection) the polymer, or material, into mold form. The injected material may surround any exposed portions of conductors, welds, first tubing, second tubing, and lead structures, but typically does not cover external portions of the contacts.

What is claimed is:

1. A lead assembly comprising:
   a plurality of conductors, each conductor of the plurality of conductors comprising a conductor first end, a conductor second end, and a conductor intermediate portion therebetween;
   a spline extending from a spline first end to a spline second end, the spline defining a plurality of walls extending radially outward from a central portion of the spline at different circumferential locations, wherein each wall of the plurality of walls has a radially outward free end, wherein adjacent walls of the plurality of walls define conductor channels therebetween, wherein the central portion of the spline defines a stylet lumen, and wherein the conductor first end of each conductor of the plurality of conductors is disposed within respective conductor channels of the conductor channels;
   a first set of contacts electrically coupled with respective conductors of the plurality of conductors at the conductor first end;
   a second set of contacts electrically coupled with respective conductors of the plurality of conductors at the conductor second end, the second set of contacts comprising a plurality of inserts defining a plurality of apertures through which the second end of respective conductors are disposed; and
   an outer lead body disposed over at least the intermediate portion of the plurality of conductors.

2. The lead assembly of claim 1, wherein the first set of contacts are disposed at a distal end of the lead assembly and configured to contact tissue and the second set of contacts are disposed at a proximal end of the lead assembly and configured to be connected to an implantable medical device.

3. The lead assembly of claim 1, further comprising a first tubing disposed around the plurality of conductors at a portion of the conductor intermediate portion, the first tubing disposed between the conductor and the outer lead body.

4. The lead assembly of claim 3, wherein the first tubing comprises heat-shrink tubing.

5. The lead assembly of claim 3, further comprising a second tubing disposed around the spline second end and a portion of the plurality of the conductors extending away from the spline second end.

6. The lead assembly of claim 5, wherein the second tubing comprises heat-shrink tubing.

7. The lead assembly of claim 5, wherein at least a portion of the second tubing overlaps a portion of the first tubing.

8. The lead assembly of claim 1, wherein each conductor of the plurality of conductors comprises a respective insulation sheath.

9. The lead assembly of claim 1, wherein the first set of contacts comprise ring electrodes.

10. The lead assembly of claim 1, wherein the first set of contacts comprise segmented electrodes, wherein the segmented electrodes comprise electrodes disposed at different positions around a perimeter of the lead assembly.

11. A method comprising:
    disposing conductors within a spline, the spline extending from a spline first end to a spline second end, the spline defining a plurality of walls extending radially outward from a central portion of the spline at different circumferential locations, wherein each wall of the plurality of walls has a radially outward free end, wherein adjacent walls of the plurality of walls define conductor channels therebetween, wherein the central portion of the spline defines a stylet lumen, and wherein conductors extend from a conductor first end to a conductor second end and have a conductor intermediate portion therebetween, wherein disposing the conductors includes disposing the conductor first end of the conductors within the conductor channels;
    electrically coupling a first set of contacts with the conductors at the conductor first end;
    disposing the conductor second end of each of the plurality of conductors through respective apertures of the second set of contacts;
    electrically coupling each of the plurality of conductors with the respective second set of contacts; and
    disposing an outer lead body over the conductors.

12. The method of claim 11, wherein the first set of contacts are disposed at a distal end and configured to contact tissue and the second set of contacts are disposed at a proximal end of the lead assembly and configured to contact an implantable medical device.

13. The method of claim 11, further comprising disposing a first heat-shrink tubing around a portion of the conductor intermediate portion, and heating the first heat shrink tubing.

14. The method of claim 13, further comprising disposing a second heat-shrink tubing around a portion of the conductor intermediate portion, and heating the second heat shrink tubing.

15. The method of claim 14, wherein disposing the second heat-shrink tubing around a portion of the conductor intermediate portion includes disposing the second heat-shrink tubing over the first heat-shrink tubing and the second tubing overlaps a portion of the first tubing.

16. The method of claim 11, further comprising molding an outer lead body over the conductors, over the first tubing, between the first set of electrodes, and between the second set of electrodes.

17. A lead assembly comprising:
    a plurality of conductors, each conductor of the plurality of conductors comprising a conductor first end, a conductor second end, and a conductor intermediate portion therebetween;
    a spline extending from a spline first end to a spline second end, the spline defining a plurality of walls extending radially outward from a central portion of the spline at different circumferential locations, wherein each wall of the plurality of walls has a radially outward free end, wherein adjacent walls of the plurality of walls define conductor channels therebetween, wherein the central portion of the spline defines a stylet lumen, and wherein the conductor first end of each conductor of the plurality of conductors is disposed within respective conductor channels of the conductor channels;

a first set of contacts electrically coupled with respective conductors of the plurality of conductors at the conductor first end;

a second set of contacts electrically coupled with respective conductors of the plurality of conductors at the conductor second end, the second set of contacts comprising a plurality of inserts defining a plurality of apertures through which the second end of respective conductors are disposed;

a first tubing disposed around the plurality of conductors at a portion of the conductor intermediate portion, the first tubing disposed between the conductor and the outer lead body;

a second tubing disposed around the spline second end and a portion of the plurality of the conductors extending away from the spline second end; and an outer lead body disposed over at least the intermediate portion of the plurality of conductors.

18. The lead assembly of claim 17, wherein the second tubing overlaps a portion of the first tubing.

19. The lead assembly of claim 17, wherein the first tubing comprises heat-shrink tubing.

20. The lead assembly of claim 17, wherein the second tubing comprises heat-shrink tubing.

\* \* \* \* \*